(12) United States Patent
Meddad et al.

(10) Patent No.: US 10,202,505 B2
(45) Date of Patent: Feb. 12, 2019

(54) POLYPROPYLENE AND ARTICLES THEREOF

(71) Applicant: SAUDI BASIC INDUSTRIES CORPORATION, Riyadh (SA)

(72) Inventors: Abderrahman Meddad, Riyadh (SA); Hesham A. Al-Shobilly, Riyadh (SA); Mansour I. Taftaf, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/606,022

(22) Filed: May 26, 2017

(65) Prior Publication Data

US 2017/0260379 A1 Sep. 14, 2017

Related U.S. Application Data

(62) Division of application No. 14/133,209, filed on Dec. 18, 2013, now Pat. No. 9,718,902.

(30) Foreign Application Priority Data

Dec. 20, 2012 (EP) .................................. 12008478

(51) Int. Cl.
| | | |
|---|---|---|
| C08L 23/14 | (2006.01) | |
| B29C 49/00 | (2006.01) | |
| B29C 51/00 | (2006.01) | |
| B29C 47/00 | (2006.01) | |
| B29C 45/00 | (2006.01) | |
| C08F 110/06 | (2006.01) | |
| C08J 5/00 | (2006.01) | |
| G01K 17/00 | (2006.01) | |
| G01N 11/00 | (2006.01) | |
| G01N 30/00 | (2006.01) | |

(52) U.S. Cl.
CPC .......... *C08L 23/14* (2013.01); *B29C 45/0001* (2013.01); *B29C 47/0004* (2013.01); *B29C 49/0005* (2013.01); *B29C 51/002* (2013.01); *C08F 110/06* (2013.01); *C08J 5/00* (2013.01); *G01K 17/00* (2013.01); *G01N 11/00* (2013.01); *G01N 2030/486* (2013.01); *Y10T 428/139* (2015.01); *Y10T 428/1397* (2015.01)

(58) Field of Classification Search
CPC ............. C08L 23/14; G01N 2030/486; B29C 47/0004; B29C 45/0001; B29C 51/002; B29C 49/0005
See application file for complete search history.

(56) References Cited

U.S. PATENT DOCUMENTS

| | | |
|---|---|---|
| 5,262,573 A | 11/1993 | Smith et al. |
| 6,759,500 B1 | 7/2004 | Dolle et al. |
| 8,008,417 B2 | 8/2011 | Brant et al. |
| 2014/0178617 A1 | 6/2014 | Meddad |

FOREIGN PATENT DOCUMENTS

| | | | |
|---|---|---|---|
| EP | 0849287 A1 | 6/1998 | |
| EP | 0 942 013 A1 * | 9/1999 | |
| EP | 1661917 A1 | 5/2006 | |
| WO | 9632427 A1 | 10/1996 | |
| WO | 0123441 A1 | 4/2001 | |
| WO | 2006025917 A2 | 3/2006 | |
| WO | WO 2006/025917 A2 * | 3/2006 | .............. C08F 10/06 |
| WO | 2006056338 A1 | 6/2006 | |
| WO | 2007134851 A1 | 11/2007 | |

OTHER PUBLICATIONS

"Collection of Reports of Study on Olefin Polymerization Catalyst and Process," Dalian Institute of Chemical Physics, Chinese Academy of Sciences, Polyolefin Team, Science Press, (1979) 4 Pages.
Chinese Search Report for Chinese Application No. 201380066328.7; Filing Date: Dec. 19, 2013; 11 Pages.
Extended European Search Report; European Application No. 12008478.5; dated May 7, 2013; 4 Pages.
Periodic System of Elements; Handbook of Chemistry & Physics; 70th Edition, CRC Press; 1989-1990; 1 Page.
Ser Van Der Ven; "Polypropylene and Other Polyolefins: Polymerization and Characterization"; Studies in Polymer Science 7; 1990; 11 Pages.
International Search Report for International Application No. PCT/EP2013/077407; International Filing Date: Dec. 19, 2013; dated Feb. 18, 2014; 4 Pages.
Written Opinion of the International Searching Authority for International Application No. PCT/EP2013/077407; International Filing Date: Dec. 19, 2013; dated Feb. 18, 2014; 3 Pages.

* cited by examiner

*Primary Examiner* — Robert D. Harlan
(74) *Attorney, Agent, or Firm* — Cantor Colburn LLP

(57) ABSTRACT

The invention relates to a process for the preparation of polypropylene having: a molecular weight of 450,000-950,000, a molecular weight distribution of 3-6, and xylene soluble content of 2-6 wt %, by converting propylene into the polypropylene without pre-polymerization in the presence of a polymerization catalyst under a condition where the volume ratio of $H_2$ to propylene is at most 0.0020, wherein the catalyst comprises a catalyst component and a co-catalyst, wherein the catalyst component is obtained by a process wherein a compound with formula $Mg(OAlk)_xCl_y$, wherein x is larger than 0 and smaller than 2, y equals 2−x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor.

20 Claims, No Drawings

POLYPROPYLENE AND ARTICLES THEREOF

CROSS REFERENCE TO RELATED APPLICATIONS

This application is a Divisional of U.S. application Ser. No. 14/133,209, filed Dec. 18, 2013, and claims priority to European Application No. 12008478.5, filed Dec. 20, 2012, the contents of which are incorporated herein in their entirety by reference.

The invention is directed to a process for the polymerization of propylene in the presence of a polymerization catalyst. The invention is also directed to polypropylene obtainable by the process. The invention is also directed to a process for forming an article from the polypropylene and the article obtainable thereby.

Polypropylene (PP) is considered as a mixture of macromolecular chains with various molecular weight and structures. Therefore, modifying the molecular structure of the polypropylene may have a large influence on its flowability and physical-mechanical properties. However, PP having a very high melt viscosity is more difficult to process using conventional extrusion or injection molding.

An example of PP having a very high melt viscosity is so-called ultrahigh molecular weight polypropylene (UHMWPP). Presently, the existing UHMWPP cannot be processed by conventional processing methods such as blow molding. The main application is in fiber using gel spinning method. The only way for the UHMWPP to be processed by conventional processing methods is to mix the UHMWPP granules with other less viscous components or to add solvent (plasticizer) in order to reduce the effect of very high viscosity. In some cases, it requires modification of the existing processing equipment where higher torque is required.

U.S. Pat. No. 8,008,417 discloses a UHMWPP having a molecular weight greater than about $1.5 \times 10^6$, a molecular weight distribution of 2.5 to 7 and a melt flow rate at 230° C. of less than 0.01 dg/minute. The UHMWPP is made using Ziegler-Natta catalysts without the addition of $H_2$. Propylene is first pre-polymerized before being polymerized into the final UHMWPE.

WO2006056338 discloses a process for the polymerization of propylene using a catalyst comprising a catalyst component obtained by a process wherein a compound with formula $Mg(OAlk)_xCl_y$ wherein x is larger than 0 and smaller than 2, y equals 2−x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor. WO2006056338 does not mention the molecular weight of the propylene obtained by the process in general and does not mention (ultra) high molecular weight polypropylene.

It is an objective of the present invention to provide a process for obtaining polypropylene with a high molecular weight which allows processing by conventional processing method such as blow molding, without requiring special processing equipment.

The present invention provides a process for the preparation of polypropylene having a molecular weight of 450,000-950,000,
a molecular weight distribution of 3-6,
a melt flow in the range of 7-14 dg/min measured with a load of 21.6 kg at 230° C. or 0.05-2 dg/min measured with a load of 2.16 kg at 230° C.,
a xylene soluble content of 2-6 wt %
by converting propylene into the polypropylene without pre-polymerization in the presence of a polymerization catalyst under a condition where the volume ratio of $H_2$ to propylene is at most 0.0020, wherein the catalyst comprises a catalyst component and a co-catalyst, wherein the catalyst component is obtained by a process wherein a compound with formula $Mg(OAlk)_xCl_y$ wherein x is larger than 0 and smaller than 2, y equals 2−x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor.

It was surprisingly found that the combination of the specific catalyst, the low hydrogen polymerization condition and the polymerization without a pre-polymerization step resulted in polypropylene with the optimal molecular weight and melt flow. The polypropylene obtained according to the present invention can advantageously be processed using conventional processing methods. The term "without pre-polymerization" is herein understood to mean as normally used in the art, i.e. the final polypropylene having the above-described properties is obtained directly from the propylene monomer. The propylene monomer is not first reacted under mild conditions before the final polypropylene is obtained.

The propylene obtained has a molecular weight (Mw) of 450,000 to 900,000, preferably 700,000 to 900,000. The melt flow rate is high: 7-14 dg/min melt flow measured with a load of 21.6 kg at 230° C. or 0.05-2 dg/min measured with a load of 2.16 kg at 230° C. The molecular weight distribution of the propylene obtained according to the invention is 3-6. This molecular weight distribution is comparable to that of the polypropylene made from the same Ziegler-Natta catalyst system with the use of $H_2$, having molecular weight of 350,000 and a melt flow rate of about 3 dg/min measured with a load of 2.16 kg at 230° C. (hereinafter sometimes referred as 'the standard polypropylene'). Despite the higher molecular weight of the PP obtained according to the invention, it was found that the obtained polypropylene can be processed in conventional extrusion lines. The xylene soluble content is 2-6 wt %, preferably 3-6 wt %.

The molecular weight and the molecular weight distribution are determined by Water Gel Permeation instruments at 160° C.

The melt flow index is determined according to ASTM D1238-10.

The xylene soluble content is the amount of very low molecular weight polypropylene and the non-crystalline portion of the polypropylene resin which are dissolvable in xylene. It is measured according to ASTM D-5492, at 23° C.

The volume ratio of $H_2$ to propylene is at most 0.0020. Preferably, the volume ratio of $H_2$ to propylene is at most 0.0010, more preferably at most 0.0050. Even more preferably, the volume ratio of $H_2$ to propylene is substantially 0, i.e. no $H_2$ is added during the conversion of propylene into the final polypropylene.

Preferably, the co-catalyst is an organoaluminium alkyl compound, preferably triethyl aluminium.

Preferably, the catalyst further comprises an external donor, the external donor preferably being cyclohexylmethyldimethoxysilane.

Preferably, the molar ratio of the co-catalyst to the external donor is 0.33 to 0.52. It was found that the decrease of the external donor led to the increase in the xylene soluble, which leads to an increase in the melt flow rate of the PP obtained. This further increases the ease of its processibility. The preferred molar ratio of the co-catalyst to the external donor is 0.38-0.44.

Preferably, the polypropylene obtained according to the present invention has melt strength of at least 5, more preferably at least 6, more preferably at least 8 or more preferably at least 10 as measured by a capillary rheometer according to ASTM D3835. This may be 2-3 times higher than the standard PP made in the presence of $H_2$ as described above.

Preferably, the polypropylene obtained according to the present invention has a zero shear viscosity as measured according to ASTM D4440 of at least 10 kPa-second, more preferably at least 30 kPa-second, more preferably at least 50 kPa-second or more preferably at least 75 kPa-second at 230° C. This may be up to 18 times higher than the standard PP made in the presence of $H_2$ as described above.

Preferably, the polypropylene obtained according to the present invention has an elongational viscosity of at least 300 KPa-second, more preferably 400 KPa-second, measured by a dynamic shear test using Advanced Rheometric Expansion System (ARES) from Rheometrics Scientific. Measurement of the time-dependent elongational viscosity was carried out at 170° C. by an extensional viscosity fixture (EVF) in the ARES. Elongational rate for the measurement was 1.0. The elongational viscosity may be up to 15 times higher than the standard PP made in the presence of $H_2$ as described above.

Preferably, the polypropylene obtained according to the present invention has a crystallinity of 45-50% as measured by differential scanning calorimeter at a heating rate of 10° C./min according to ASTM D3418-08.

Preferably, the polypropylene obtained according to the present invention has a crystallization temperature of 116-119° C., as measured by a differential scanning calorimeter at a heating rate of 10° C./min according to ASTM D3418-08.

Preferably, the polypropylene obtained according to the present invention has a melting temperature of 160-163° C., as measured by differential scanning calorimeter at a heating rate of 10° C./min according to ASTM D3418-08.

The crystallization temperature, the crystallinity and the melting temperature are measured according to ASTM D3418-08 at a heating rate of 10° C./min in DSC. The sample is heated up to 200° C. (first heating) and then cooled (to measure the crystallization temperature and crystallinity) and then heated (second heating to measure the melting temperature and heat diffusion.

The PP obtained according to the invention can be processed by conventional extrusion, injection molding, thermoforming or blow molding. Accordingly, the present invention provides a process for forming an article by extrusion, injection molding, thermoforming or blow molding the polypropylene obtained according to the invention. Preferably, the temperature during the processing is increased by 10 to 15° C. compared to when processing the standard PP, for example at 240-280° C. The melt pressure may also be increased by 50% for extrusion and 10 to 15% for injection molding compared to when processing the standard PP.

A further aspect of the present invention provides the article obtainable by the process according to the present invention for forming the article, for example a film, a pipe and a container. Preferably, the container has a content of at least one gallon.

Preferably, the article has an environmental stress cracking (ESCR) of at least 800 hours, preferably at least 1000 hours at 100% Igebal. This is measured according to ASTM D1693.

Preferably, the article has a transparency measured as % haze of at least 15%, preferably at least 20% for 2 mm thickness on a BYK Gardner Haze guard Plus hazemeter in accordance with ASTM D1003.

Preferably, the article has a gloss of at least 70, more preferably at least 80 as measured according to ASTM D2457.

Preferably, the article has a ratio of impact strength (J/m) over stiffness (MPa) of at least 0.03, 0.05, more preferably at least 0.065.

Polymerization Conditions

The polymerization can be carried out in the gas phase or in the liquid phase (bulk or slurry). In the case of polymerization in the liquid phase a dispersing agent is present. Suitable dispersing agents include for instance n-butane, isobutane, n-pentane, isopentane, hexane, heptane, octane, cyclohexane, benzene, toluene, xylene and liquid propylene.

The polymerization temperature may vary within wide limits and is, for instance, between 0° C. and 120° C., preferably between 40° C. and 100° C.

The polymerization time may vary within wide limits and is, for instance, between 1-10 hours, preferably between 2.5-3.5 hours.

The pressure during the polymerization is for instance between 0.1 and 6 MPa, preferably between 0.5-3 MPa.

The polymerization can be carried out in continuous mode or batch wise. Slurry-, bulk-, and gas-phase polymerization processes, multistage processes of each of these types of polymerization processes, or combinations of the different types of polymerization processes in a multistage process are contemplated herein.

Preferably the polymerization process is a single stage gas phase process or a multistage, for instance a 2-stage, gas phase process where in each stage a gas-phase process is used.

Examples of gas-phase polymerization processes include both stirred bed reactors and fluidized bed reactor systems; such processes are well known in the art. Typical gas phase α-olefin polymerization reactor systems comprise a reactor vessel to which α-olefin monomer(s) and a catalyst system can be added and which contain an agitated bed of forming polymer particles.

Catalyst

The catalyst used in the process according to the present invention is described in WO2006056338, which is incorporated herein by reference.

The catalyst used in the process according to the present invention comprises a catalyst component obtained by a process wherein a compound with formula $Mg(OAlk)_xCl_y$, wherein x is larger than 0 and smaller than 2, y equals 2−x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor.

The catalyst has a higher activity. The obtained higher activity of the catalyst component means a higher yield of the polyolefin per gram of catalyst. The higher activity reduces the catalyst costs in the polyolefin production.

Generally, the alkyl group Alk of $Mg(OAlk)_xCl_y$ is an alkyl group with 1-8 carbon atoms. The alkyl group may be linear or branched. Preferably at least one of the Alk-groups represents an ethyl group. More preferably each Alk-group represents an ethyl group.

Preferably, the titanium tetraalkoxide contains 4-32 C-atoms. The alkoxide group of the titanium tetraalkoxide may be either linear or branched. The four alkoxide groups may be the same or differ independently. These titanium tetraalkoxide compounds may be used alone or in combination.

Preferably, at least one of the alkoxy groups in the titanium tetraalkoxide is an ethoxy group.

More preferably the titanium tetraalkoxide is titanium tetraethoxide.

Suitable alcohols include for instance a linear or branched alcohol with 1-8 C-atoms. The alcohols may be used alone or in combination.

According to a preferred embodiment of the invention the alcohol is ethanol.

Preferably the inert dispersant is a hydrocarbon solvent. The solvent may be for example an aliphatic or aromatic hydrocarbon with 1-20 C-atoms.

According to a preferred embodiment of the invention the dispersant is heptane.

The molar ratio titanium tetraalkoxide to $Mg(OAlk)_xCl_y$ may range between wide limits and is, for instance, between 0.02 and 0.5. Preferably the molar ratio is between 0.07 and 0.2.

Preferably, the molar ratio alcohol to $Mg(OAlk)_xCl_y$ is between 0.02 and 0.5. More preferably this ratio is between 0.07 and 0.2.

Preferably the temperature during the treatment of the compound with formula $Mg(OAlk)_xCl_y$ with the titanium tetraalkoxide and/or alcohol is in the range from $-10°$ C. to $50°$ C., more preferably in the range from $-5°$ C. to $40°$ C. and most preferably in the range between $0°$ C. and $30°$ C.

Preferably at least one of the reaction components is dosed in time, for instance during 0.5 to 4 hours, particularly during 1-2.5 hours.

According to a preferred embodiment of the invention the process for obtaining the catalyst component is characterized in that a compound with formula $Mg(OAlk)_xCl_y$ wherein x is larger than 0 and smaller than 2, y equals 2−x and each Alk, independently, represents an alkyl group with 1-8 carbon atoms, is contacted with a titanium tetraalkoxide in the presence of an inert dispersant to give an intermediate reaction product and wherein the intermediate reaction product is contacted with titanium tetrachloride in the presence of an internal donor.

Starting from a solid product $(Mg(OAlk)_xCl_y)$ of controlled morphology an intermediate solid reaction product $Mg(OAlk)_xCl_y.aTi(OAlk)_4$ is obtained after treatment with $Ti(Oalk)_4$ according to the equation $Mg(OAlk)_xCl_y+ TiOAlk_4 \rightarrow Mg(OAlk)_xCl_y.aTi(OAlk)_4$. wherein a depends on the selected molar ratio as described in the following. This intermediate reaction product is subsequently contacted with titanium tetrachloride in the presence of an internal donor.

If desired an alcohol may be added before, during or after the treatment with $Ti(OAlk)_4$, or a combination thereof.

In a preferred embodiment, the alcohol is first added to the compound with formula $Mg(OAlk)_xCl_y$ whereafter the tetraalkoxide is added. The alcohol and the tetraalkoxide preferably are added slowly, for instance during 0.5-4 hours, most preferably during 1-2.5 hours, each.

The $TiCl_4/Mg$ molar ratio in the contact between the intermediate product and titanium tetrachloride preferably is between 10 and 100, most preferably, between 10 and 50.

Examples of suitable internal donors include carboxylic acids, carboxylic acid anhydrides, esters of carboxylic acids, halide carboxylic acids, alcohols, ethers, ketones, amines, amides, nitriles, aldehydes, alcoholates, sulphonamides, thioethers, thioesters and other organic compounds containing a hetero atom, such as nitrogen, oxygen, sulphur and/or phosphorus.

The molar ratio of the internal donor relative to the magnesium during the treatment of the intermediate product with the titanium tetrachloride may vary between wide limits, for instance between 0.05 and 0.75.

Preferably this molar ratio is between 0.1 and 0.4.

Examples of suitable carboxylic acids are formic acid, acetic acid, propionic acid, butyric acid, isobutanoic acid, acrylic acid, methacrylic acid, maleic acid, fumaric acid, tartaric acid, cyclohexanoic monocarboxylic acid, cis-1,2-cyclohexanoic dicarboxylic acid, phenylcarboxylic acid, toluenecarboxylic acid, naphthalene carboxylic acid, phthalic acid, isophthalic acid, terephthalic acid and/or trimellitic acid.

Anhydrides of the aforementioned carboxylic acids can be mentioned as examples of carboxylic acid anhydrides, such as for example acetic acid anhydride, butyric acid anhydride and methacrylic acid anhydride.

Suitable examples of esters of carboxylic acids are formates, for instance, butyl formate; acetates, for instance ethyl acetate and butyl acetate; acrylates, for instance ethyl acrylate, methyl methacrylate and isobutyl methacrylate; benzoates, for instance methylbenzoate and ethylbenzoate; methyl-p-toluate; ethyl-☐-naphthoate and phthalates, for instance monomethyl phthalate, dibutyl phthalate, diisobutyl phthalate, diallyl phthalate and/or diphenyl phthalate.

Examples of suitable halide carboxylic acids are the halides of the carboxylic acids mentioned above, for instance acetyl chloride, acetyl bromide, propionyl chloride, butanoyl chloride, butanoyl iodide, benzoyl bromide, p-toluyl chloride and/or phthaloyl dichloride.

Examples of suitable alcohols are methanol, ethanol, butanol, isobutanol, xylenol and benzyl alcohol.

Examples of suitable ethers are diethyl ether, dibutyl ether, diisoamyl ether, anisole and ethylphenyl ether, 2,2-diisobutyl-1,3-dimethoxypropane, 2,2-dicyclopentyl-1,3-dimethoxypropane, 2-ethyl-2-butyl-1,3-dimethoxypropane, 2-isopropyl-2-isopentyl-1,3-dimethoxypropane and/or 9,9-bis(methoxymethyl) fluorene. Also, tri-ethers can be used.

Examples of other organic compounds containing a heteroatom are 2,2,6,6-tetramethyl piperidine, 2,6-dimethylpiperidine, 2-methylpyridine, 4-methylpyridine, imidazole, benzonitrile, aniline, diethylamine, dibutylamine, thiophenol, 2-methyl thiophene, isopropyl mercaptan, diethylthioether, diphenylthioether, tetrahydrofuran, dioxane, dimethylether, diethylether, anisole, acetone, triphenylphosphine, triphenylphosphite, diethylphosphate and/or diphenylphosphate.

Preferably the internal donor is dibutyl phthalate.

Most preferably the internal donor is di-n-butyl phtalate.

In the contact between the intermediate product and the titanium tetrachloride use is preferably made of an inert dispersant. The dispersant may be selected for example from the groups of aliphatic or aromatic hydrocarbon compounds with, for instance, 4-20 C-atoms. The dispersant preferably is chosen such that virtually all side products are dissolved in the dispersant. Suitable dispersants include for example aliphatic and aromatic hydrocarbons and halogenated aromatic solvents with for instance 4-20 C-atoms. Suitable examples are toluene, xylene, benzene, heptane and chlorobenzene.

The reaction temperature during the contact between the intermediate product and the titanium tetrachloride is preferably between 50° C. and 150° C., most preferably between 60° C. and 120° C. At higher or lower temperatures the activity of the catalyst component prepared according to the process of the invention becomes lower. The obtained reaction product is purified, usually with an inert aliphatic or aromatic hydrocarbon or halogenated aromatic compound, to obtain the catalyst component of the invention. If desired, the reaction and subsequent purification may be repeated one or more times.

The preparation of the magnesium containing support having the formula $Mg(OAlk)_xCl_y$ is well known in the art and several methods are for instance described in U.S. Pat. No. 5,262,573 and references cited therein.

In a preferred embodiment such a magnesium containing support is prepared for instance as described in WO-A-96/32427 and WO-A-01/23441 wherein the magnesium containing support is obtained by:

a) a Grignard formation step wherein metallic magnesium is contacted with an organic halide RX, where R is an organic group, preferably an aromatic group, containing for instance up to 20 carbon atoms and X is a halide, whereupon the resulting dissolved first reaction product is separated from the solid residual products and whereafter, b) an alkoxy group or aryloxy group containing silane compound is contacted with the obtained first reaction product whereupon the precipitate formed is purified. Preferably in step b), a stirred reactor is used.

The Grignard formation step in the process for the preparation of the catalyst component of the invention is carried out by contacting metallic magnesium with an organic halide RX.

All forms of metallic magnesium may be used. Preferably use is made of finely divided metallic magnesium, for example magnesium powder. To obtain a fast reaction it is preferable to heat the magnesium under nitrogen prior to use. In the organic halide RX, R is an organic group preferably containing from 1 up to 20 carbon atoms and X preferably is chlorine or bromine.

Examples of the organic group R are methyl, ethyl, n-propyl, i-propyl, n-butyl, i-butyl, t-butyl, hexyl, octyl, phenyl, tolyl, xylyl, mesityl and benzyl.

Combinations of two or more organic halides RX can also be used. Preferably R represents an aromatic group, for instance a phenyl group.

Preferably RX represents chlorobenzene.

The magnesium and the organic halide RX can be reacted with each other without the use of a separate dispersant; the organic halide RX is then used in excess. The organic halide RX and the magnesium can also be brought into contact with one another in the presence of an inert dispersant. Examples of suitable dispersants include aliphatic, alicyclic or aromatic dispersants containing from 4 up to 20 carbon atoms.

Preferably, an excess of chlorobenzene is used as the organic halide RX. Thus, the chlorobenzene serves as dispersant as well as organic halide RX.

Preferably, in the Grignard formation step also an ether is present in the reaction mixture.

Examples of suitable ethers include diethyl ether, diisopropyl ether, dibutyl ether, diisobutyl ether, diisoamyl ether, diallyl ether, tetrahydrofuran (THF) and anisole.

Preferably, the ether is dibutyl ether and/or diisoamyl ether.

The organic halide/ether ratio acts upon the activity of the catalyst component. More generally it acts upon the polymerization performance and the catalyst morphology. The volume ratio organic halide to ether, for instance the ratio chlorobenzene/dibutyl ether, may vary within wide limits, for example between 75:25 and 35:65.

When the organic halide/ether ratio, for instance the chlorobenzene/dibutyl ether ratio, decreases, the bulk density of the polyolefine powder prepared with the aid of the catalyst component becomes lower and when the organic halide/ether ratio increases, the amount of the dissolved first reaction product becomes lower. The ratio at which the best results are obtained depends on the specific reactants and conditions chosen and can easily be determined by the skilled person. For instance when chlorobenzene and dibutylether were used the best results were obtained when the chlorobenzene/dibutyl ether volume ratio was between 70:30 and 50:50.

Small amounts of iodine and/or alkyl halides can be added to cause the reaction between the metallic magnesium and the organic halide RX to proceed at a higher rate. Examples of suitable alkyl halides are butyl chloride, butyl bromide and 1,2-dibromoethane. When the organic halide RX is an alkyl halide, iodine or 1,2-dibromoethane is preferably used.

The reaction temperature for the Grignard formation step may range for instance between 20° C. and 150° C. and the reaction times may range for instance between 0.5 and 20 hours.

After the Grignard formation is completed, the dissolved first reaction product is separated from the solid residual products.

Preferably in step b) the silane compound and first reaction product are introduced simultaneously to a mixing device in order to improve the morphology of the catalyst particles, especially of the larger catalyst particles, as described in WO-A-01/23441. Here, 'morphology' does not only refer to the shape of the catalyst particles, but also to the particle size distribution, its fine content, powder flowability and the bulk density of the catalyst particles. Moreover, it is well known that the polyolefin powder produced in the polymerization by using a catalyst component has the same morphology as the catalyst component (the so-called "replica effect"; see for instance S. van der Ven, Polypropylene and other Polyolefins, Elsevier 1990, p. 8-10). Accordingly almost round polymer particles are obtained with a length/diameter ratio (1/d) smaller than 2 and good powder flowability.

"Simultaneous introduction" means the introduction of the first reaction product and the silane compound in such a way that the molar ratio Mg/Si does not substantially vary during the introduction of these compounds to the mixing device.

The silane compound and first reaction product can be continuously or batch-wise introduced to the mixing device. Preferably, the silane compound and the first reaction product are introduced continuously to the mixing device.

The mixing device can have various forms; the mixing device can be a mixing device in which the silane compound is premixed with the first reaction product, the mixing device can also be the reactor in which the reaction between the silane compound and the first reaction product takes place.

Preferably, the silane compound and the first reaction product are premixed before the mixture is introduced to the reactor for step b). In this way a catalyst component is formed with a morphology that leads to polymer particles with the best morphology (high bulk density, narrow particle size distribution, (virtually) no fines, excellent flowability).

The Si/Mg molar ratio during step b) may vary within wide limits for instance from 0.2 to 20. Preferably, the Si/Mg molar ratio is from 0.4 to 1.0.

Preferably the alkoxy group or aryloxy group containing silane is a compound or a mixture of compounds with the general formula $SiR^1{}_nOR^2{}_{4-n}$, wherein n is 0, 1, 2 or 3, preferably n is 0 or 1, each $R^1$, independently, represents an alkyl, alkenyl or aryl group, optionally containing one or more hetero atoms for instance O, N, S or P, with, for instance, 1-20 C-atoms, and each $R^2$, independently, represents an alkyl or aryl group, optionally containing one or more hetero atoms for instance O, N, S or P, with, for instance, 1-20 C-atoms.

Preferably, the silane is tetraethoxysilane.

The period of premixing may vary between wide limits, for instance 0.1 to 300 seconds. Preferably premixing is performed during 1 to 50 seconds.

The temperature during the premixing is not critical and may for instance range between 0 and 80° C.; preferably the temperature is between 10° C. and 50° C.

The reaction between the silane compound and the first reaction product may, for instance, take place at a temperature between −20° C. and 100° C.; preferably at a temperature of from 0° C. to 80° C.

The product obtained with the reaction between the silane compound and the first reaction product, is usually purified by rinsing with an inert solvent, for instance a hydrocarbon solvent with for instance 1-20 C-atoms. It is very suitable to be used as starting material in the process of the present invention for the preparation of a catalyst compound.

The catalyst used in the process of the present invention comprises the catalyst component as described above and a co catalyst. Preferably, the catalyst also comprises an external donor.

It is an advantage of the present invention that the amount of metal residues in the obtained polymer is reduced.

Generally, the co catalyst is an organometallic compound containing a metal from group 1, 2, 12 or 13 of the Periodic System of the Elements (Handbook of Chemistry and Physics, 70th Edition, CRC Press, 1989-1990).

Preferably, the co catalyst is an organoaluminium compound. The organoaluminium compound may be, for instance, a compound having the formula $AlR^3{}_3$, wherein each $R^3$ independently represents an alkyl group with, for instance, 1-10 C-atoms or an aryl group with, for instance, 4-20 C-atoms. Suitable examples of an organoaluminium compound are organoaluminium alkyl compounds such as trimethyl aluminium, triethyl aluminium, ethyl-di-methyl aluminium, triisobutyl aluminium, methyl-ethyl-butyl aluminium and/or trioctyl aluminium.

According to a preferred embodiment of the invention the co catalyst is triethyl aluminium.

Examples of possible external donors are for instance the compounds described above as the internal donors that can be used in the preparation of the catalyst component. As external donor also organo-silicon compounds can be used. Mixtures of external donors can also be used.

Examples of organo-silicon compounds that are suitable as external donor are compounds or mixtures of compounds with the general formula $SiR^4{}_nOR^5{}_{4-n}$, wherein n is 0, 1 or 3, preferably n is 1 or 2, each $R^4$, independently, represents an alkyl, alkenyl or aryl group, optionally containing one or more hetero atoms for instance O, N, S or P, with, for instance, 1-20 C-atoms, and each $R^5$, independently, represents an alkyl or aryl group, optionally containing one or more hetero atoms for instance O, N, S or P, with, for instance, 1-20 C-atoms, for instance tetramethoxysilane, tetraethoxysilane, methyltrimethoxysilane, methyltributoxysilane, ethyltriethoxysilane, phenyltriethoxysilane, diethyldiphenoxysilane, n-propyltriethoxysilane, diisopropyldimethoxysilane, diisobutyldimethoxysilane, n-propyltrimethoxysilane, cyclohexylmethyldimethoxysilane, icyclopentyldimethoxysilane, isobutylisopropyldimethoxylsilane, phenyltrimethoxysilane, diphenyldimethoxysilane, trifluoropropylmethyldimethoxysilane, bis(perhydroisoquinolino)dimethoxysilane, dicyclohexyldimethoxysilane, dinorbornyldimethoxysilane, di(n-propyl)dimethoxysilane, di(iso-propyl)dimethoxysilane, di(n-butyl)dimethoxysilane and/or di(iso-butyl)dimethoxysilane.

Preferably the organo-silicon compound is n-propyltrimethoxysilane, cyclohexylmethyldimethoxysilane, di(iso-propyl)dimethoxysilane or di(iso-butyl)dimethoxysilane.

The molar ratio of the metal in the co catalyst relative to the Ti during the polymerization may vary for instance from 5 to 2000. Preferably this ratio is between 50 and 300.

The aluminium/donor molar ratio in the polymerization mixture preferably is between 0.1 and 200; more preferably between 1 and 100.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will now be further illustrated with below described experiments.

1. Catalyst Preparation

In all examples below, the catalyst prepared by the following process was used.

A. Grignard Formation Step

A stainless steel reactor of 9l volume was filled with magnesium powder 360 g. The reactor was brought under nitrogen. The magnesium was heated at 80° C. for 1 hour, after which a mixture of dibutyl ether (1 liter) and chlorobenzene (200 ml) was added. Then iodine (0.5 g) and n-chlorobutane (50 ml) were successively added to the reaction mixture. After the colour of the iodine had disappeared, the temperature was raised to 94° C. Then a mixture of dibutyl ether (1.6 liter) and chlorobenzene (400 ml) was slowly added for 1 hour, and then 4 liter of chlorobenzene was slowly added for 2.0 hours. The temperature of reaction mixture was kept in interval 98-105° C. The reaction mixture was stirred for another 6 hours at 97-102° C. Then the stirring and heating were stopped and the solid material was allowed to settle for 48 hours. By decanting the solution above the precipitate, a solution of phenylmagnesiumchloride reaction product A has been obtained with a concentration of 1.3 mol Mg/l. This solution was used in the further catalyst preparation.

B. Preparation of the first intermediate reaction product (Mg(OAlk)$_x$Cl$_y$)

The solution of reaction product of step A (360 ml, 0.468 mol Mg) and 180 ml of a solution of tetraethoxysilane (TES) in dibutyl ether (DBE), (55 ml of TES and 125 ml of DBE), were cooled to 10° C., and then were dosed simultaneously to a mixing device of 0.45 ml volume supplied with a stirrer and jacket. Dosing time was 360 min. Thereafter the premixed reaction product A and the TES-solution were introduced to a reactor. The mixing device (minimixer) was cooled to 10° C. by means of cold water circulating in the minimixer's jacket. The stirring speed in the minimixer was 1000 rpm. The stirring speed in reactor was 350 rpm at the beginning of dosing and was gradually increased up to 600 rpm at the end of dosing stage.

On the dosing completion the reaction mixture was heated up to 60° C. and kept at this temperature for 1 hour. Then the stirring was stopped and the solid substance was allowed to settle. The supernatant was removed by decanting. The solid substance was washed three times using 500 ml of heptane. As a result, a pale yellow solid substance, reaction product B (the solid first intermediate reaction product; the support), was obtained, suspended in 200 ml of heptane. The average particle size of support was 22 μm and span value (d90–d10)/d50=0.5.

C. Preparation of the Second Intermediate Reaction Product

Support activation was carried out as described in Example IV of WO/2007/134851 to obtain the second intermediate reaction product.

In inert nitrogen atmosphere at 200° C. a 250 ml glass flask equipped with a mechanical agitator is filled with slurry of 5 g of reaction product B dispersed in 60 ml of heptane. Subsequently a solution of 0.22 ml ethanol (EtOH/Mg=0.1) in 20 ml heptane is dosed under stirring during 1 hour. After keeping the reaction mixture at 200 C for 30 minutes, a solution of 0.79 ml titanium tetraethoxide (TET/Mg=0.1) in 20 ml of heptane was added for 1 hour.

The slurry was slowly allowed to warm up to 300 C for 90 min and kept at that temperature for another 2 hours. Finally the supernatant liquid is decanted from the solid reaction product (the second intermediate reaction product; activated support) which was washed once with 90 ml of heptane at 30° C.

D. Preparation of the Catalyst Component

A reactor was brought under nitrogen and 125 ml of titanium tetrachloride was added to it. The reactor was heated to 90° C. and a suspension, containing about 5.5 g of activated support in 15 ml of heptane, was added to it under stirring. The reaction mixture was kept at 90° C. for 10 min. Then add 0.866 g of ethyl acetate (EA/Mg=0.25 mol). The reaction mixture was kept for 60 min (I stage of catalyst preparation). Then the stirring was stopped and the solid substance was allowed to settle. The supernatant was removed by decanting, after which the solid product was washed with chlorobenzene (125 ml) at 900 C for 20 min. Then the washing solution was removed by decanting, after which a mixture of titanium tetrachloride (62.5 ml) and chlorobenzene (62.5 ml) was added. The reaction mixture was kept at 900° C. for 30 min (II stage of catalyst preparation), after which the stirring was stopped and the solid substance was allowed to settle. The supernatant was removed by decanting, after which a mixture of titanium tetrachloride (62.5 ml) and chlorobenzene (62.5 ml) was added. Then 0.5 g of 9,9-bis-methoxymethyl-9H-fluorene (flu) (flu/Mg=0.05 mol) in 3 ml of chlorobenzene was added to reactor and the temperature of reaction mixture was increased to 1150° C. The reaction mixture was kept at 1150° C. for 30 min (III stage of catalyst preparation), after which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 1150° C. for 30 min (IV stage of catalyst preparation), after which the solid substance was allowed to settle. The supernatant was removed by decanting and the solid was washed five times using 150 ml of heptane at 600 C, after which the catalyst component, suspended in heptane, was obtained.

The catalyst has the following composition:

TABLE 1

| Ti wt % | Mg wt % | Mg/Ti MR | EtO wt % | DNBP wt % | D10 | D50 | D90 | Mean |
|---|---|---|---|---|---|---|---|---|
| | | | | | | Microns | | |
| 2 | 19.6 | 19.3 | 0.44 | 7.8 | 11.1 | 19 | 28.3 | 19 |

Ti = Titanium loading on the catalyst
Mg = Magnesium
EtO = Ethanol
DNBP = Internal Donor content
D10 = 10$^{th}$ percentile of catalyst particle size.
Mean = Average catalyst particle size 2. Polymerization in Pilot Plant Propylene was polymerized using the catalyst component obtained according to step D. The polymerization was performed continuously in a gas phase reactor in the presence of a catalyst comprising the catalyst component according to step D, triethylaluminium and cyclohexylmethyldimethoxysilane. The polymerization period was 3 hours. The concentration of the catalyst component was 4 cc/hr; the concentration of triethylaluminium was 0.07 kg/hr. The concentration of cyclohexylmethyldimethoxysilane is shown in the Table 3, along with the molar ratio of triethylaluminium to cyclohexylmethyldimethoxysilane.

The reactor used for the polymerization was a Unipol Gas Phase Pilot Plant Reactor. This is a continuous reactor which can produce PP resin up to 20 kg/hr as a maximum production capacity. In this example, the production rate was 15 kg/hr. The reactor conditions are described in Table 2:

TABLE 2

| REACTOR CONDITIONS | |
|---|---|
| Bed Temperature (° C.) | 63 |
| Reactor Pressure (Barg) | 29 |
| C3 Partial Pressure (Bara) | 24 |
| Bed wt. (mbar) | 30 |
| SGV (superficial gas velocity) (m/s) | 0.34 |
| Catalyst Flow (cc/hr) | 4 |
| TEAL flow (kg/hr) | 0.07 |
| Carrier Flow (kg/hr) | 4 |
| Production Rate (kg/hr) | 15 |

Four experiments were performed. In experiment 1 (comparative), the reaction was performed under the presence of H$_2$. The volume ratio of H$_2$ to propylene was 0.0038. In example 2, the reaction was performed under a reduced amount of H$_2$. The volume ratio of H$_2$ to propylene was 0.019. In example 3 and 4, the reaction was performed without H$_2$.

The productivity, bulk density (BD), xylene solubles content, average particle size, melt flow index measured at 2.16 kg, number average molecular weight (Mn) and weight average molecular weight (Mw) are presented in Table 3. The molecular weight and molecular weight distribution were characterized utilizing Waters 2000 Alliance Gel Permeation Chromatograph at 160° C. The melt flow index was measured utilizing Zwick 4106 melt index instrument. The xylene solubles content was measured according to ASTM D-5492, at 23° C. Resin bulk density and average particle size were measured according to ASTM D792 and ASTM D4513-11, respectively.

TABLE 3

| Reference | $H_2/C_3$ Vol. Ratio | Kg/hr | External donor conc. mol ratio co-catalyst to external donor | Productivity Kg PP/g cat. hr | BD g/l | XS wt % | APS microns |
|---|---|---|---|---|---|---|---|
| Ex 1 (comp) | 0.0038 | 0.35 | 0.33 | 25 | 431 | 2.9 | 743 |
| Ex 2 | 0.0019 | 0.32 | 0.36 | 23 | 434 | 3.4 | 871 |
| Ex 3 | 0 | 0.28 | 0.41 | 22.9 | 460 | 3.1 | 888 |
| Ex 4 | 0 | 0.22 | 0.52 | 17.5 | 441 | 5.8 | 588 |

| Reference | MFI (2.16 kg) g/10 min | Mn g/mole | Mw g/mole | MWD |
|---|---|---|---|---|
| Ex 1 (comp) | 3.9 | 62,500 | 359,500 | 5.8 |
| Ex 2 | 1.8 | 79,000 | 451,500 | 4.2 |
| Ex 3 | 0.09 | 140,250 | 911,000 | 5.4 |
| Ex 4 | 0.2 | 139,000 | 806,000 | 5.8 |

Properties of the polyethylene of Ex. 1 (comp.) and Ex. 3 were measured.

The melt strength was measured using capillary rheometer equipped with pulley according to ASTM D 3835. The melt strength of the sample of Ex.3 was around 10, which was 2-3 times higher than the sample of Ex. 1.

The zero shear viscosity was measured according to ASTM D4440. The zero shear viscosity of the sample of Ex. 3 was 75 KPa-second, which was about 18 times higher than that of the sample of Ex. 1. The zero shear viscosity of the sample of Ex. 2 and of Ex. 4 was also measured and was found to be about 9 KPa-second and 38 KPa-second, respectively.

The elongational viscosity was measured using Advanced Rheometric Expansion System (ARES) equipped with an extensional viscosity fixture (EVF). The elongational viscosity of the sample of Ex. 3 was 400 KP-second at 170° C., which was about 15 times higher than that of the sample of Ex. 1.

The crystallization temperature, the crystallinity and the melting temperature were measured according to ASTM D3418-08 at a heating rate of 10° C./min in DSC. The sample was heated up to 200° C. (first heating) and then cooled (to measure the crystallization temperature and crystallinity) and then heated (second heating to measure the melting temperature and heat diffusion. TA DSC-Q-1000, Q2000 and Q20 instruments. The crystallinity level of the samples of Ex.3 was about 48%, which was 3% lower than the sample of Ex. 1. The crystallization and melting temperatures of the sample of Ex.3 were 118° C. and 163° C., respectively. These temperatures were very similar to the samples of Ex.1. The same trend was observed when using a lower heating rate of about 2° C./min from 50° C. to 260° C.

3. Processing of Polypropylene Into Article
3.1 Extrusion

The polypropylene obtained by Experiments 1 and 3 were processed using a co-rotating twin screw extruder for continuous compounding of polymeric materials equipped with a hopper feeder: Brabender-TSE 35/17D.

Polypropylene from comparative experiment 1 was processable with an output of 20 kg/h, at a melt temperature of 220° C. and a melt pressure of 960 psi. For processing polypropylene from experiment 3, the melt temperature was about 10° C. higher and the melt pressure was about 50% higher compared to processing polypropylene from comparative experiment 1.

3.2 Blow Molding

The polypropylene obtained by Example 3 was processed by blow molding. The polypropylene obtained by Example 3 was stabilized by using phenolic and phosphites antioxidants and acid scavenger (Irganox 101, Irgafos 168 and DHT-4A). The PP base resin and additives were blended in a Henshel mixer for 5 minutes prior to extrusion. Sample was melt compounded on a 30-mm twin screw extruder (ZSK 30 type form MPM) at melt temperature 227° C. and screw speed of 200 rpm. The molten PP was processed on Battenfeld blow molding machine to produce bottles (0.5 L). The melt temperature was 240° C.

It is therefore shown that the polypropylene having a relatively high molecular weight can be processed by conventional equipment. The article formed had good properties such as good environmental stress cracking (ESCR) of about >1000 hours at 100% Igebal, higher transparency measured as % haze of about 20% for 2 mm thickness on a BYK Gardner Haze-gard Plus hazemeter in accordance with ASTM D1003, good gloss >80 according to ASTM D2457 and lower weight (180 g).

3.3 Injection Molding

The polypropylene obtained by Ex. 1 (Comp) and Ex 3 were also injection molded by using Battenfeld injection molding machine with a general-purpose screw to produce samples for measuring flexural modulus and Izod impact strength. The injection pressure was 800 bar and the temperature was 200-225° C., the nozzle temperature being 225° C. The injection speed was 10 mm/s and the injection time was 2.50 second.

The stiffness and the impact strength were measured according to ASTM D1043-D and ASTM D256, respectively. The sample from PP of Ex. 1 (Comp.) had a stiffness of 1370 MPa and an impact strength of 26 J/m, whereas the sample from PP of Ex. 3 had a stiffness of 1320 MPa and an impact strength of 90 J/m. The sample according to the invention had an excellent Impact strength/stiffness balance.

The invention claimed is:

1. Polypropylene comprising:
   a Mw of 450,000 to 950,000;
   a molecular weight distribution of 3 to 6;
   a melt flow in the range of 7 to 14 dg/min measured with a load of 21.6 kg at 230° C. or 0.05 to 2 dg/min measured with a load of 2.16 kg at 230° C.; and
   a xylene soluble content of 2 to 6 wt %; and
   wherein the polypropylene has a crystallization temperature of 116 to 119° C.

2. The polypropylene according to claim 1, wherein the polypropylene has a melt strength of at least 5 as measured by a capillary viscometer according to ASTM D3835.

3. The polypropylene according to claim 1, wherein the polypropylene has a zero shear viscosity of at least 10 kPa-second at 230° C. as measured according to ASTM D4440.

4. The polypropylene according to claim 1, wherein the polypropylene has an elongational viscosity of at least 300 KPa-second at 170° C. as measured using Advanced Rheometric Expansion System equipped with EVF.

5. Polypropylene comprising:
   a Mw of 450,000 to 950,000;
   a molecular weight distribution of 3 to 6;
   a melt flow in the range of 7 to 14 dg/min measured with a load of 21.6 kg at 230° C. or 0.05 to 2 dg/min measured with a load of 2.16 kg at 230° C.; and
   a xylene soluble content of 2 to 6 wt %; and
   wherein the polypropylene has a crystallinity of 45 to 50%.

6. Polypropylene comprising:
   a Mw of 450,000 to 950,000;
   a molecular weight distribution of 3 to 6;
   a melt flow in the range of 7 to 14 dg/min measured with a load of 21.6 kg at 230° C. or 0.05 to 2 dg/min measured with a load of 2.16 kg at 230° C.; and
   a xylene soluble content of 2 to 6 wt %; and
   wherein the polypropylene has a melting temperature of 160 to 163° C., as measured by differential scanning calorimeter according to ASTM D3418-08 at a heating rate of 10° C./min.

7. The polypropylene according to claim 1, wherein the polypropylene has a xylene soluble content of 3 to 6 wt %.

8. A process for forming an article comprising extruding, injection molding, thermoforming, or blow molding the polypropylene of claim 1.

9. The process according to claim 8, wherein the article is formed at a temperature of 240 to 280° C.

10. The article obtained by the process of claim 8.

11. The article according to claim 10, wherein the article has an environmental stress cracking (ESCR) of at least 800 hours at 100% Igebal as measured according to ASTM D1693.

12. The article according to claim 10, wherein the article has a transparency measured as % haze of at least 15% for 2 mm thickness on a BYK Gardner Haze-gard Plus hazemeter in accordance with ASTM D1003.

13. The article according to claim 10, wherein the article has a gloss of at least 70 according to ASTM D2457.

14. The article according to claim 10, wherein the article has a ratio of impact strength (J/m) over stiffness (MPa) of at least 0.03.

15. The article according to claim 10, wherein the article is a film, a pipe or a container.

16. The polypropylene according to claim 5, wherein the polypropylene has a melt strength of at least 5 as measured by a capillary viscometer according to ASTM D3835.

17. The polypropylene according to claim 5, wherein the polypropylene has a zero shear viscosity of at least 10 kPa-second at 230° C. as measured according to ASTM D4440.

18. The polypropylene according to claim 6, wherein the polypropylene has a melt strength of at least 5 as measured by a capillary viscometer according to ASTM D3835.

19. The polypropylene according to claim 6, wherein the polypropylene has a zero shear viscosity of at least 10 kPa-second at 230° C. as measured according to ASTM D4440.

20. The polypropylene according to claim 6, wherein the polypropylene has an elongational viscosity of at least 300 KPa-second at 170° C. as measured using Advanced Rheometric Expansion System equipped with EVF.

* * * * *